(12) United States Patent
Lavelle et al.

(10) Patent No.: US 9,532,795 B2
(45) Date of Patent: *Jan. 3, 2017

(54) BUTTON RELEASE HANDLE (71) Applicant: Cook Medical Technologies LLC, Bloomington, IN (US)

(72) Inventors: Shay J. Lavelle, Annacotty (IE); James Giltinan, Corbally (IE)

(73) Assignee: Cook Medical Technologies LLC, Bloomington, IN (US)

( * ) Notice: Subject to any disclaimer, the term of this patent is extended or adjusted under 35 U.S.C. 154(b) by 328 days.

This patent is subject to a terminal disclaimer.

(21) Appl. No.: 14/490,860

(22) Filed: Sep. 19, 2014

(65) Prior Publication Data

US 2015/0000480 A1    Jan. 1, 2015

Related U.S. Application Data

(63) Continuation of application No. 13/484,953, filed on May 31, 2012, now Pat. No. 8,840,630.

(Continued)

(51) Int. Cl.
*A61B 17/3207*    (2006.01)
*A61B 17/3205*    (2006.01)
(Continued)

(52) U.S. Cl.
CPC ..... *A61B 17/2909* (2013.01); *A61B 17/00234* (2013.01); *A61B 17/32056* (2013.01);
(Continued)

(58) Field of Classification Search
CPC ............ A61B 17/2909; A61B 17/32056; A61B 17/00234; A61B 2017/292; A61B 2017/00858
See application file for complete search history.

(56) References Cited

U.S. PATENT DOCUMENTS 5,456,683 A    10/1995    Fritzsch et al.
5,630,818 A    5/1997    Del Rio et al.
(Continued)

FOREIGN PATENT DOCUMENTS

EP    0 688 535 A1    5/1995
EP    0 688 535 A1    12/1995
(Continued)

OTHER PUBLICATIONS

Extended European Search Report for EP 16 16 9696, dated Sep. 7, 2016, 9 pp.

(Continued)

*Primary Examiner* — David B Thomas
(74) *Attorney, Agent, or Firm* — Brinks Gilson & Lione (57) ABSTRACT

A handle for receiving an elongate medical device is provided. The handle includes a housing defining an elongate hollow interior portion, the hollow portion defining a first portion proximate the distal end and the aperture, a second portion. A core is slidably disposed within the interior portion and includes a ramp portion extending from an outer surface of the core at an oblique angle to the longitudinal axis, and two or more arms extending outwardly from a proximal end of the core and biased toward an extended configuration where a proximal end of each arm extends radially outside of an outer surface of the core, wherein the two or more arms combine to define the proximal opening. A button is movably disposed within the aperture substantially blocking communication with the hollow portion through the aperture, comprising an inclined surface that slidably engages the ramp surface.

25 Claims, 6 Drawing Sheets

Related U.S. Application Data (60) Provisional application No. 61/497,358, filed on Jun. 15, 2011.

(51) Int. Cl.
    *A61B 17/29* (2006.01)
    *A61B 17/00* (2006.01)

(52) U.S. Cl.
    CPC ............... *A61B 2017/0046* (2013.01); *A61B 2017/00858* (2013.01); *A61B 2017/292* (2013.01)

(56) References Cited

U.S. PATENT DOCUMENTS

| | | | |
|---|---|---|---|
| 5,976,143 | A | 11/1999 | McCue |
| 6,007,560 | A | 12/1999 | Gottliev et al. |
| 6,053,934 | A | 4/2000 | Andrews et al. |
| 6,197,001 | B1 | 3/2001 | Wilson et al. |
| 6,299,624 | B1 | 10/2001 | Cuschieri et al. |
| 6,527,780 | B1 | 3/2003 | Wallace et al. |
| 6,652,537 | B2* | 11/2003 | Mercereau ............ A61B 17/221 606/113 |
| 6,676,668 | B2* | 1/2004 | Mercereau ............ A61B 17/221 606/1 |
| 6,764,499 | B2 | 7/2004 | Honey et al. |
| 6,862,776 | B2 | 3/2005 | Chen |
| 6,984,213 | B2 | 1/2006 | Horner et al. |
| 7,419,501 | B2* | 9/2008 | Chiu .................... A61F 2/95 623/1.12 |
| 8,287,448 | B2* | 10/2012 | Schaaf ................. A61B 1/0051 600/114 |
| 9,439,672 | B2* | 9/2016 | Scheller ............ A61B 17/2909 606/1 |
| 2002/0128678 | A1 | 9/2002 | Petersen |
| 2008/0312671 | A1 | 12/2008 | Riles et al. |
| 2009/0026682 | A1 | 1/2009 | Smith et al. |
| 2010/0130996 | A1 | 5/2010 | Doud et al. |
| 2011/0125132 | A1 | 5/2011 | Krolik et al. |
| 2012/0046679 | A1 | 2/2012 | Patel et al. |
| 2012/0053574 | A1* | 3/2012 | Murray, III ............... A61F 2/95 606/1 |
| 2014/0031844 | A1 | 1/2014 | Kusleika |

FOREIGN PATENT DOCUMENTS

| | | |
|---|---|---|
| JP | 2005 323878 | 11/2005 |
| WO | WO 96/10962 | 4/1996 |
| WO | WO 01/10290 A2 | 2/2001 |
| WO | WO 01/87166 A2 | 11/2001 |
| WO | WO 02/41932 A2 | 5/2002 |
| WO | WO 2005/120628 A2 | 12/2005 |

OTHER PUBLICATIONS

Office Communication pursuant to Article 94(3) EPC from European Patent Office in corresponding EPO patent application for "Button Release Handle", App. No. 12172077.5, filed Jun. 14, 2012, communication dated May 5, 2015, 5 pp.

Office Communication under Rule 71(c) EPC from European Patent Office in corresponding EPO patent application for "Button Release Handle", App. No. 12172077.5, dated Apr. 19, 201, 40 pp.

European Search Report for 12 172 077.5, dated Apr. 25, 2013.

\* cited by examiner

BUTTON RELEASE HANDLE

CROSS-REFERENCE TO RELATED APPLICATIONS

This application is a continuation of U.S. nonprovisional application Ser. No. 13/484,953 filed on May 31, 2012, issued as U.S. Pat. No. 8,840,630, which claimed priority from U.S. Provisional Application Ser. No. 61/497,358, filed on Jun. 15, 2011, the entirety of which are each hereby fully incorporated by reference herein.

TECHNICAL FIELD

The field of the disclosure is that of medical and surgical instruments, and in particular, medical and surgical instruments intended primarily for minimally-invasive procedures. These instruments typically have a small diameter for entering body spaces or orifices of limited size and often are sold with or are usable with handles to assist with the manipulation of the device.

BRIEF SUMMARY

A first representative embodiment of the disclosure is provided. The embodiment includes a handle for receiving an elongate medical device, such as a basket, a snare, forceps and the like. The handle includes a housing defining an elongate hollow interior portion that allows communication through an open distal end and through an aperture disposed upon a side surface of the housing. The hollow portion defines a first portion proximate the distal end and the aperture, a second portion that is disposed proximally of the first portion with an inner diameter less than an inner diameter of the first portion, and a third portion that is disposed proximally of the second portion with an inner diameter larger than the inner diameter of the second portion. A core is slidably disposed within the interior portion and includes a central lumen disposed therethrough along a longitudinal axis between a distal opening and a proximal opening. The core includes a ramp portion extending from an outer surface of the core at an oblique angle to the longitudinal axis, and two or more arms extending outwardly from a proximal end of the core and biased toward an extended configuration where a proximal end of each arm extends radially outside of an outer surface of the core. The two or more arms combine to define the proximal opening. A button is movably disposed within the aperture and substantially blocks communication with the hollow portion through the aperture. The button includes an inclined surface that slidably engages the ramp surface, wherein engagement of the ramp and inclined surfaces establishes a normal position of the core within the housing, such that the arms are aligned with the second portion of the hollow portion to urge the arms inwardly away from their extended configuration and minimize the size of the proximal opening.

Yet another representative embodiment of the disclosure is provided. The embodiment includes a handle for removably receiving an elongate medical device, such as a basket, a snare, forceps and the like. The handle includes an elongate rigid housing enclosing a central hollow portion disposed along at least a substantial portion of the housing and an aperture disposed upon a side surface of the housing communicating with the hollow portion. The hollow portion maintains a first inner diameter for a majority of a length of the hollow portion. The hollow portion additionally includes a thin smaller inner diameter portion at a proximal portion of the hollow portion. A slidable core is disposed within the hollow portion of the housing, and includes an elongate core lumen disposed therethrough. The core lumen is sized to receive a shaft of an elongate medical device; the core further includes a ramp surface disposed thereon. A collet is disposed within the hollow portion and movable with movement of the core within the housing. The collet comprises a collet lumen in registration with the core lumen, and two or more arms attached to a proximal end of the collet at a first portion thereon and each with a second portion that is biased radially outward outside of an outer surface of the collet. The slidable core and the collet are each biased distally such that the second portion of each arm contacts the smaller diameter portion to urge each arm radially inward from its biased configuration toward a restrained configuration.

Yet still another representative embodiment of the disclosure is provided. The embodiment includes a handle for removably receiving an elongate medical device, such as a basket, a snare, forceps and the like. The handle includes a housing that is configured to receive the proximal portion of the elongate medical device within a lumen provided along the longitudinal axis of the housing. The housing includes a void that extends from a side surface of the housing and into the lumen. The void receives a button therethrough that is movably mounted within the housing and operable by a user holding the handle. The button includes a button lumen that is normally at least partially offset from the housing lumen, but may be placed in coaxial registration with the housing lumen by depressing the button toward the lumen of the housing. When an elongate member of a medical device is threaded through the lumen and the button lumen, the elongate member becomes engaged at the distal and proximal ends of the button lumen with the housing to prevent relative movement of the elongate member within the housing lumen due to frictional forces. When the button is fully depressed, the button is in registration with the housing lumen and the elongate member may be easily removed from (or manipulated within) the button lumen and therefore the housing.

Yet another representative embodiment of the disclosure is provided. The embodiment includes a handle for removably receiving an elongate medical device, such as a basket, a snare, forceps and the like. The handle includes an elongate rigid housing enclosing a central hollow portion disposed along at least a substantial portion of the housing and an aperture disposed upon a side surface of the housing communicating with the hollow portion. The hollow portion maintains a first inner diameter for a majority of a length of the hollow portion. The hollow portion additionally includes a thin smaller inner diameter portion at a proximal portion of the hollow portion. A slidable core is disposed within the hollow portion of the housing, and includes an elongate core lumen disposed therethrough. The core lumen is sized to receive a shaft of an elongate medical device; the core further includes a ramp surface disposed thereon. A collet is disposed within the hollow portion and movable with movement of the core within the housing. The collet includes two or more arms that contribute to a rear opening into the collet lumen, wherein the motion of the arms radially outward increases a diameter of the rear opening. The core lumen and the collet lumen are configured to slidably receive the shaft of an elongate medical device, such that a proximal end of the shaft extends through the rear opening. An elongate portion of a medical device is provided as a kit with the handle, the elongate portion comprises a proximal tip and a transition portion connected distally of the proximal tip and formed with a smaller diameter than a diameter of the proximal tip, wherein the transition portion is configured to be received within the collet lumen, and the proximal tip extends through the rear opening.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION

Figures 1, 1A, 1B:
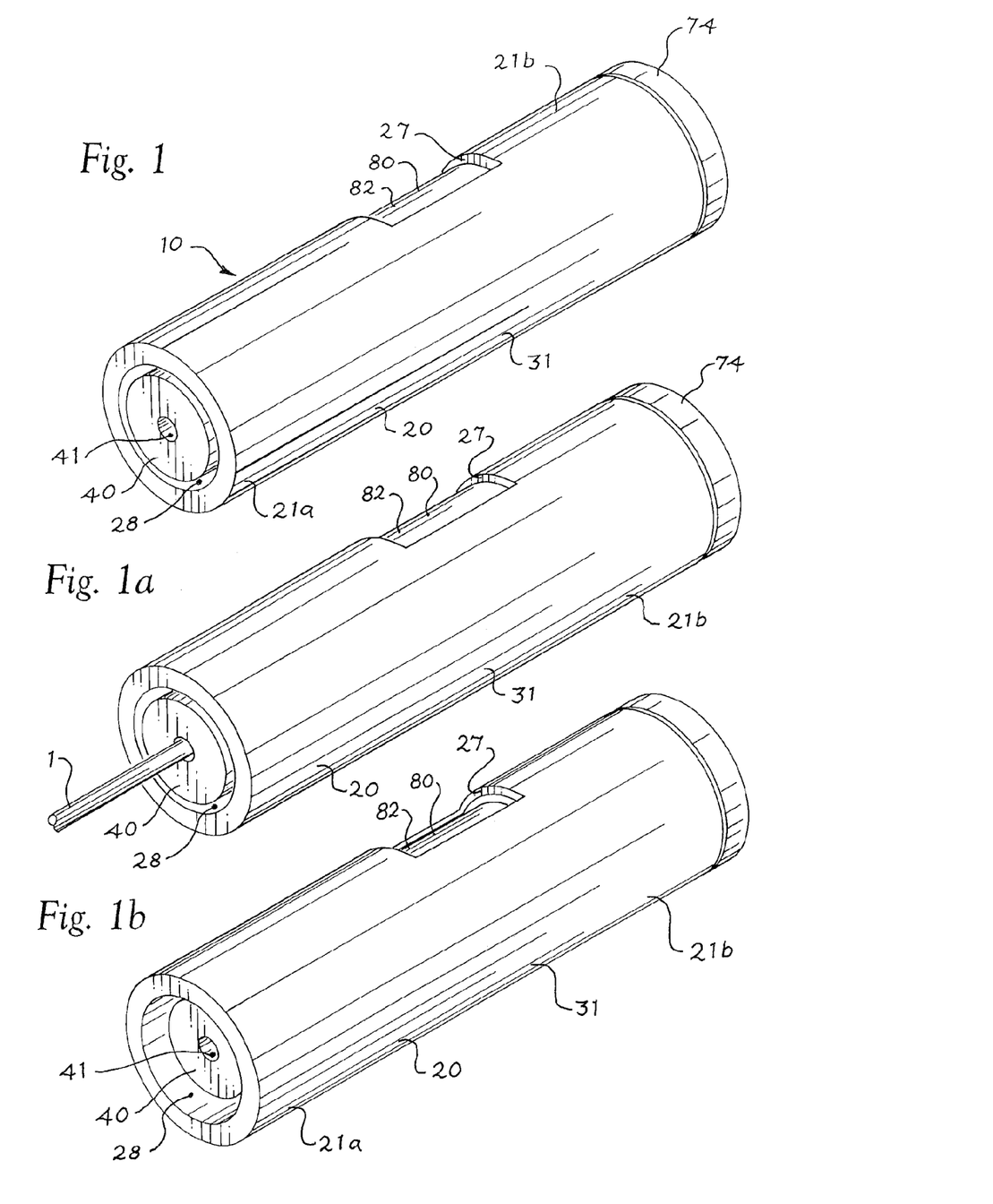
FIG. 1 is a perspective view of a representative handle of the disclosure.
FIG. 1a is the view of FIG. 1 with a medical device received within the handle.
FIG. 1b is the view of FIG. 1 with the button depressed.

Turning now to FIGS. 1-5, a handle 10 is provided that is configured to releasably receive a proximal portion 1 of an elongate medical device, such as a basket, a snare, or the like. The handle 10 includes a housing 20 and a core 40 slidably disposed within an internal, hollow portion 23 of the housing 20. The hollow portion 23 may extend from an open distal end 21a of the housing 20 to an open proximal end 21b of the housing 20, while in other embodiments, the hollow portion 23 may extend from an open distal end 21a to a closed proximal end. In embodiments with an open proximal end 21b, the proximal end 21b may be ultimately closed with a cap 74 that is removably mounted to the proximal end of the housing 20, with a threaded connection, a snap fit or press fit connection, or by another attachment structure known in the art. In still other embodiments, the distal end of the housing 20 may be substantially closed, with only a central opening configured to receive the proximal end 1 of a medical device therethrough. As shown in FIG. 1, in embodiments with an open distal end 21a of the housing 20, the proximal end 1 of a medical device may be threaded directly into a lumen 41 of the core 40, which extends along the entire length of the core 40, and in some embodiments along the longitudinal axis 100 (FIG. 2) of the core 40 (which may or may not be co-linear with the longitudinal axis of the housing 20, or the handle 10).

Figure 2:
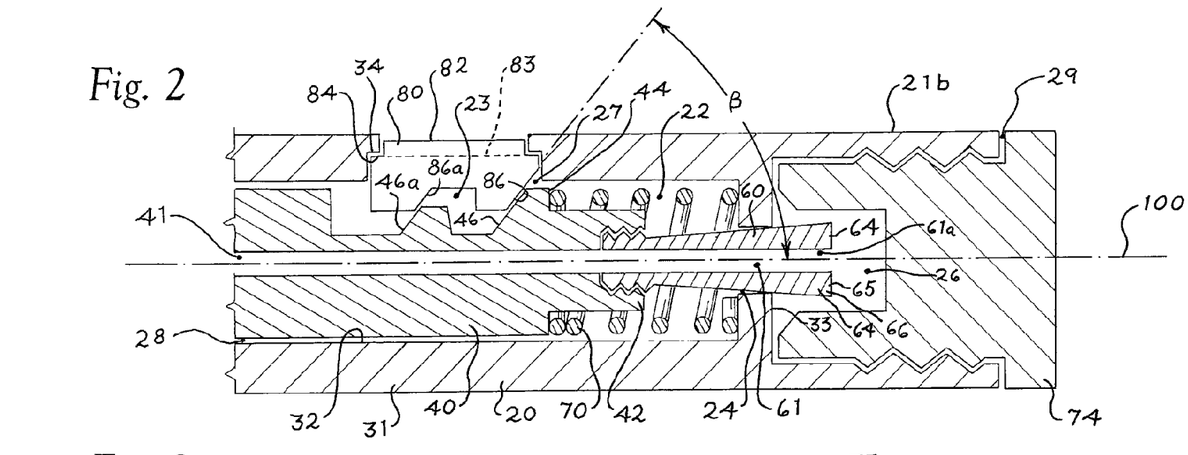
FIG. 2 is a cross-sectional view of the handle of FIG. 1 showing the handle in the normal configuration.
Figure 3:
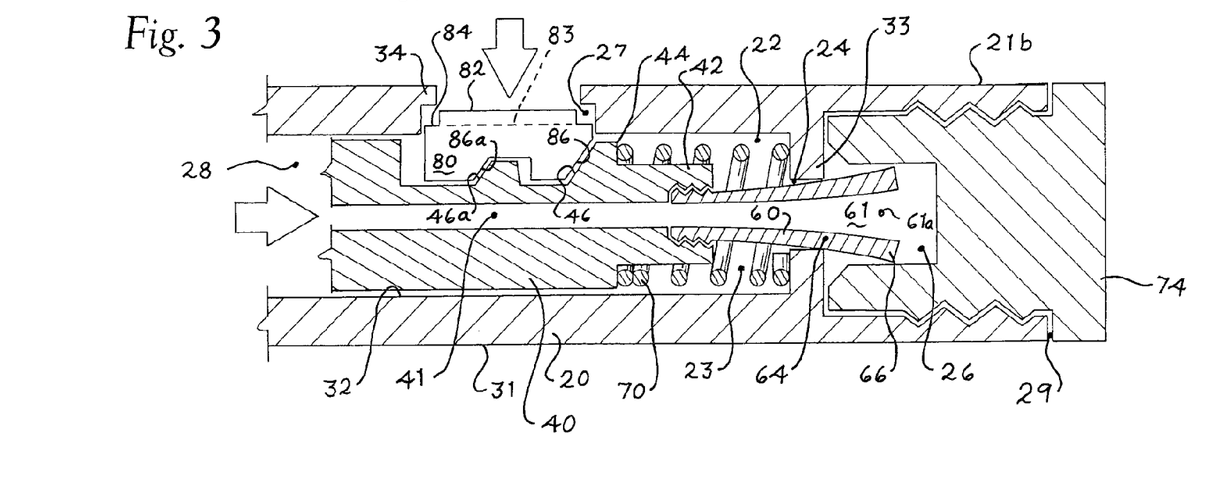
FIG. 3 is the view of FIG. 2 showing the button depressed.
Figure 4:
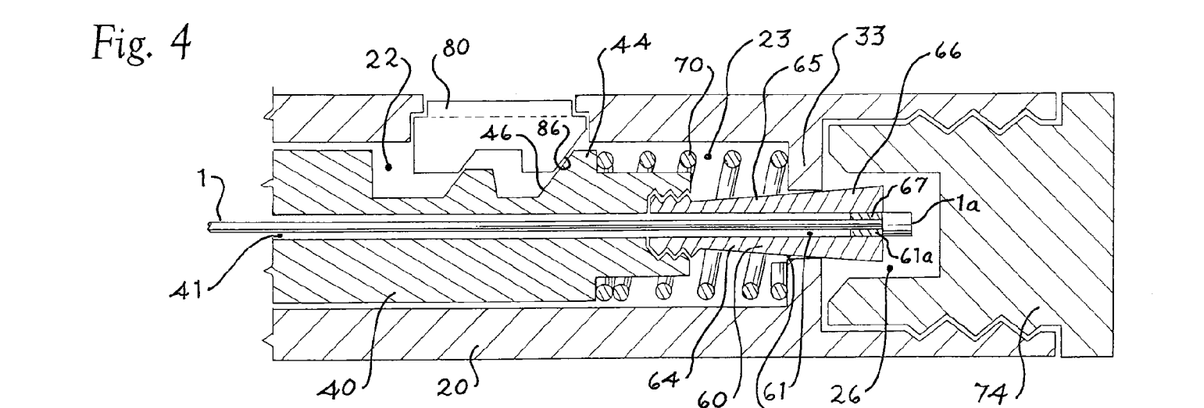
FIG. 4 is the view of FIG. 2 showing a medical received within the handle with the handle in the normal configuration.
Figure 5:
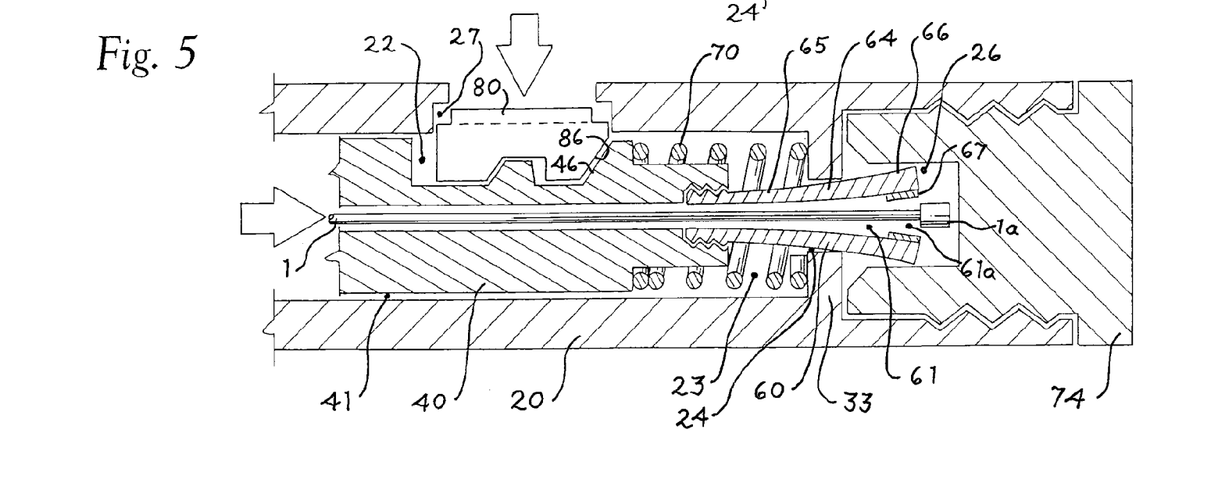
FIG. 5 is the view of FIG. 3 showing a medical device inserted within the handle with the button depressed.

As best shown with combined reference to FIGS. 2 and 3, the core 40 is slidable longitudinally within the housing 20 as urged by movement of a button 80 that extends through an aperture 27 in the housing 20 and is operable by a user that is holding the housing 20 with a single hand, and in some embodiments, is operable by simply pressing the thumb of the user's hand on the button 80 to compress it further into the aperture 27. As will be discussed in additional detail below, depressing the button 80 urges the core 40 proximally within the hollow portion 23 of the housing 20 to a removal configuration (FIG. 3), and releasing the depressed button 80 cases the core 40 to return to its normal position (FIG. 2).

The housing 20 is an elongate, substantially rigid member that may be configured to be held and manipulated with a single hand of a user and is configured to allow the user to insert and remove a proximal elongate portion 1 of a flexible medical device therein. The housing 20 may be a single molded piece, or may be assembled from two or more clam-shell halves that are fixed together after the housing 20 is assembled. The housing 20 has an outer surface 31 that may be ergonomically and geometrically adapted for the comfortable receipt and manipulation by the user's hand. In some embodiments, the housing 20 may be formed with a smooth or rough outer surface 31, may have a plurality of projections for comfortable receipt of a user's fingers, or other design features known in the art. The housing 20 may be made from a rigid plastic material, such as ABS or may be made from a metal, or may be made from a composite material. One of ordinary skill in the art will appreciate that while a plurality of materials are available for use in the housing 20 (as well as the other components of the handle 10, discussed below), material selection will be based upon various factors such as cost, weight, strength, availability, manufacturability and the like.

The housing 20 is configured to define an inner hollow portion 23, which is an open internal volume within an inner surface 32 of the housing 20. The hollow portion 23 includes a distal, first portion 22 that extends from an open distal end 21a (in embodiments including this structure) or at least a distal portion of the housing 20 and extends along a majority of the length of the housing 20. The first portion 22 is defined at a first inner diameter and is in communication with an aperture 27 defined through a portion of the side wall of the housing 20. In some embodiments, the aperture 27 may be of a constant shape and size through the thickness of the side wall of the housing 20, while in other embodiments the aperture may have a first cross-section at the outer surface 31 of the housing 20 and form a larger cross section inwardly from the outer surface 31 of the housing 20. The area of the housing side wall distinguishing the larger and smaller cross-section of the housing is defined as the step 34 (FIG. 2).

The hollow portion 23 includes a second portion 24 proximal of the first portion 22, which has a smaller inner diameter than the inner diameter of the first portion 22. The second portion 24 may be defined from a wall 33 that extends radially inward into the hollow portion 23 from the inner surface 32 of the housing 20 along the entire inner circumference of the hollow portion 23, the majority of the inner circumference, or at predetermined positions within the inner circumference, to substantially reduce the inner diameter of the hollow portion 23. As discussed below in additional detail, the wall 33 of the housing 20, and the second portion 24 of the hollow portion 23 defined therefrom, is configured to urge the arms 64 of a collet 60 (in conjunction with the core 40) together to minimize the size of the rear opening 61a into the collet lumen 61. As discussed below, in some embodiments, the collet 60 and core 40 may be formed as a monolithic piece, such that the arms 64 are a part of the core 40, although operation of the device with a monolithic core 40 and collet 60 is substantially the same as the embodiment where the core 40 and collet 60 are different elements joined together. For the sake of brevity, embodiments with separate collet 60 and core 40 fixed together will be discussed, but one of ordinary skill in the art will understand that the structure disclosed herein can be freely substituted with a monolithic core 40 and collet 60.

The hollow portion 23 may further include a third portion 26 proximal of the second portion 24, which has a larger inner diameter than the inner diameter of the second portion 24. In some embodiments, the inner diameter of the third portion 26 may be substantially the same as the inner diameter of the first portion 22, while in other embodiments, the inner diameter of the third portion 26 may be different. The third portion 26 of the hollow portion 23 is configured to allow space for the second ends 66 of each of the plurality of arms 64 of the collet 60 to extend radially away from each other and radially away from the outer surface of the collet 60, with the radial outward motion of the second ends 66 of the arms 64 increasing the size of the proximal opening 61a into the collet lumen 61. As mentioned above, the housing 20 may include a proximal opening 29, which is normally closed by a cap 74 that is fixably retained upon the housing 20 to close the proximal opening, but is removable to allow for assembly of the handle 10. The cap 74 may be friction fit within the housing, threaded upon the housing, or in some embodiments where the housing is a single molded piece (or formed from two clamshell halves), the cap 74 may be formed integrally with the remainder of the housing 20.

The core 40 is an elongate member that is slidably received within the hollow portion 23 of the housing 20. The core 40 has a lumen 41 that extends therethrough, which may extend collinearly with the longitudinal axis 100 through the core 40, while in other embodiments, the core lumen 41 extends in an offset manner from the longitudinal axis. In some embodiments, the core lumen 41 extends through the core 40 in parallel to the direction of sliding motion of the core 40 through the hollow portion 23. The core lumen 41 is configured to receive the proximal end 1 of an elongate medical device therethrough and is either accessible to the user through the open distal end 28 of the housing 20, or through a hole in the distal end 21a of the housing 20 and in registration with the core lumen 41. The core lumen 41 is configured to receive the proximal portion 1 of a medical device therethrough, to allow free, limited friction, sliding of the proximal portion 1 therealong, including an enlarged proximal tip 1a (FIGS. 4-5) that may be present upon the elongate medical device.

The core 40 may include an upstanding surface 44 at or near the proximal end of the core 40, that is configured to engage one end of a spring 70, such as a compression spring, that may be disposed within the hollow portion 23 and between the upstanding surface 44 and the wall 33 of the housing 20. In some embodiments, the spring 70 may be installed in a compressed manner (with the handle 10 in the normal configuration) such that the core 40 constantly feels a force urging the core 40 distally within the hollow portion 23. The core 40 includes one or more ramp surfaces 46 (46a) that extend from the core 40 at an oblique angle β with respect to the longitudinal axis 100 of the core 40. The one or more ramp surfaces 46 (46a) are configured to make sliding contact with inclined surfaces 86 (86a) of the button 80 as discussed below. In some embodiments, a portion of the core 40 defining a ramp surface 46 (or 46a when provided) may also define the upstanding member 44. The spring 70 biases the core 40 in the distal direction to urge continuous contact between the ramp surface(s) 46 (46a) of the core 40 and the inclined surface(s) 86 (86a) of the button 80. The contact between the ramp and inclined surfaces 46, 86 establishes the avenue for transfer of force from the button 80 to the core 40 (and ultimately to the arms 64 of the collet 60), but also prevents further distal motion of the core 40 within the hollow portion 23, which allows for embodiments of the handle 10 with an open front portion on the housing 20 without the core 40 sliding distally out of the housing 20.

The button 80 is a member that is received within the aperture 27 in the side surface of the housing 20 and is configured to engage the core 40, as discussed above. Specifically, the button 80 includes one or more inclined surfaces 86 (86a) that extend radially into the hollow portion 23 of the housing 20 to engage the opposed ramp surfaces 46 (46a) of the core 40. In some embodiments, the inclined surface(s) may be disposed at substantially the same angle β with respect to the longitudinal axis 100 of the core 40, such that the opposed ramp and inclined surfaces 46, 86 make sliding contact with respect to each other. The angle β is configured to impart a proximally directed force upon the core 40 for moving the core 40 proximally within the hollow portion 23 of the housing 20 as the button 80 is urged into the hollow portion 23 of the housing. The angle β is determined by an optimization of at least two competing factors, i.e. the amount of available horizontal motion of the core 40 with a set vertical displacement of the button 80 (e.g. smaller angles β provide for greater horizontal displacement with respect to a set amount of vertical displacement), competing with the larger frictional forces observed with smaller angles β (due to a larger vertical component of the force vector acting as a normal force upon the surface contact). Angles around 45 degrees are believed to be suitable for this design, as well as angles within the range of about 30 degrees to about 60 degrees, inclusive thereof. Of course, the specific angle β chosen will be optimized based upon the required horizontal movement of the core 40 needed and the vertical movement of the button 80 available, and those of ordinary skill in the art will be able to choose an optimal angle β based upon the specific geometric (size, shape), and physical design of the handle 10 with reference to this specification. Similarly, in embodiments where the proximal end 1 of the medical device includes an enlarged tip 1a (FIGS. 4-5), the proximal opening 61a of the collet 60 needs to be large enough to allow the tip 1a to pass when the button 80 is fully pressed, but still retain the proximal end 1 of the medical device when the handle 10 is in the normal configuration, thereby requiring a larger range of motion of the arms 64 of the collet 60 and potentially a larger range of horizontal motion of the core 40 than embodiments where the proximal end 1 of the medical device does not have an enlarged tip (1a).

In some embodiments, the button 80 defines a ledge 84 that surrounds all or a portion of an extended central portion of the button 80. The ledge 84 is a cross-sectional portion of the button that includes a larger cross-sectional area than the top surface 82 of the button 80, and may be formed along a plane 83 (FIG. 2) formed below and in parallel (or at a constant offset distance in embodiments where the top surface 82 is not planer) to the top surface 82 of the button. As best shown in FIG. 2, the ledge 84 of the button engages a step 34 formed in the housing 20 to prevent the button 80 from falling through or being removable from the aperture 27 in the housing. As can be understood, the combined geometry of the ledge 84, the button 80, and the step 34 define the range of upward motion of the button 80 within the housing 20, and also, based upon engagement between the opposed ramp and inclined surfaces 46, 86, defines the limit of core 40 motion in the distal direction.

As shown in FIG. 2, the top surface 82 of the button 80 may be recessed below the outer surface 31 of the housing 20 to prevent spurious and unintended motion of the button 80 (and therefore unintended release of the device from the handle 10). Specifically, the recessed positioning of the button 80 below the outer surface 31 of the housing 20 minimizes the chance of the button 80 being engaged and depressed if the handle 10 is inadvertently dropped or mishandled.

As mentioned above, the collet 60 is disposed proximal of the core 40 and is configured to translate within the housing 20 with motion of the core 40. In some embodiments, the collet 60 may be removably fixed to the core 40 (such as with a threaded connection as shown in FIGS. 2 and 3, or alternatively, the collet 60 may be insert molded to the core, press fit, or fixed thereto with adhesive or fasteners), while in other embodiments, the collet 60 may be monolithically formed with the core 40. The collet 60 includes a collet lumen 61 that extends through the collet 60 and in registry with the core lumen 41 to receive the elongate proximal end 1 of a medical device disposed therethrough. The collet lumen 61 extends to a proximal end through a rear opening 61a that is defined by the second ends 66 of a plurality of arms 64 that extend from the collet 60. Each of the plurality of arms 64 include a first portion fixed to the collet 60 and a second portion 66 that extend from the collet 60. The second ends 66 of each arm 64 are biased away from the outer surface of the collet 60 and from the second ends 66 of the other arms 64, such that the second ends 66 are urged to establish a relatively large rear opening 61a into the collet lumen 61 when the arms 64 are free to move to a biased outward configuration (FIG. 3), i.e. when the arms 64 are within the third portion 26 of the hollow portion 23.

As shown in FIG. 2, the collet arms 64 are normally maintained in a narrowed configuration within the second portion 24 of the hollow portion 23, due to the biasing force of the spring 70 upon the core 40. The wall 33 of the housing 20 urges the plurality of arms 64 toward the outer surface of the remainder of the collet 60 and toward each other, such that the size of the rear portion 61a of the collet lumen 61 is minimized to retain the proximal end 1 of a medical device within the collet lumen 61. In embodiments where the proximal tip 1a of the medical device is enlarged, the combined second ends 66 of the arms 64 define a rear opening 61a that is smaller than the cross-section of the proximal tip 1a to prevent distal movement of the medical device when the handle is in the normal configuration. In these embodiments, the diameter of the remainder of the core lumen 41 and the collet lumen 61 is larger than the largest anticipated proximal tip 1a of the medical device to allow the proximal tip 1a to be threaded through the lumens 41, 61. The collet 60 and the collet arms 64 may be made from metal or plastic and contain enough elasticity to deform into a compressed state and return into an expanded state (normal bias position), without suffering permanent disfiguration.

In some embodiments, the inner surface of the second end 66 of one, some, or all of the collet arms 64 may have a retention structure 67 (FIGS. 4 and 5) that assists with maintaining the second end 1 of a medical device inserted within the handle 10 in addition to the normal inward force imparted upon the proximal end 1 of the device from the compressed arms. For example, the inner surface may be coated with a high friction material to enlarge the frictional force felt upon the proximal end 1 of the device disposed within the collet lumen 61. In other embodiments, the inner surface may have a thicker material to cause the plurality of arms 64 to collectively press upon the proximal end 1 of the device. Alternatively, the inner surface may include a plurality of teeth that collectively dig or bite into the proximal end of the device.

The core 40 and collet 60 are movable proximally within the hollow portion 23 of the housing when the button 80 is depressed by the user. The proximal movement of the collet 60 causes the extended second ends 66 of the plurality of arms 64 to move radially outward away from each other as they slide proximally past the wall 33 in the housing 20 and into the third portion 26 of the hollow portion 23, due to the outward biasing force imparted upon the arms 64 during manufacture. As shown with reference to FIG. 3, the proximal motion of the arms 64 and radially outward motion of the second ends 66 of the arms 64 causes the size of the rear opening 61a of the collet lumen 61 to increase to a size where the proximal end 1 of the medical device is no longer engaged by the arms 64 and is freely removed from the collet lumen 61 and the handle 10 (and also allows the proximal portion 1 of the medical device to be slid between the arms and through the rear opening 61a in the collet lumen 61 when the device is initially being loaded into the handle 10).

Figure 6:
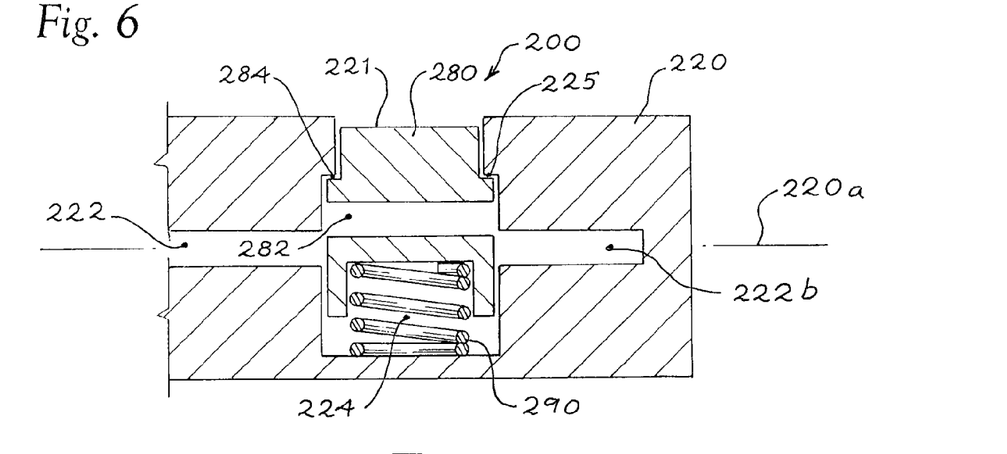
FIG. 6 is a cross-sectional view of an alternate embodiment of a handle showing the handle in a normal configuration without receipt of an elongate device therewithin.
Figure 7:
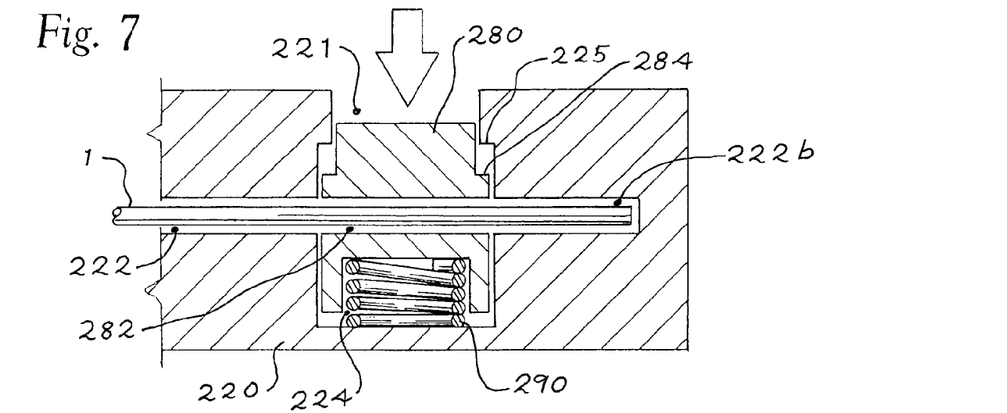
FIG. 7 is the view of FIG. 6 with the button fully depressed receiving an elongate device therewithin.
Figure 8:
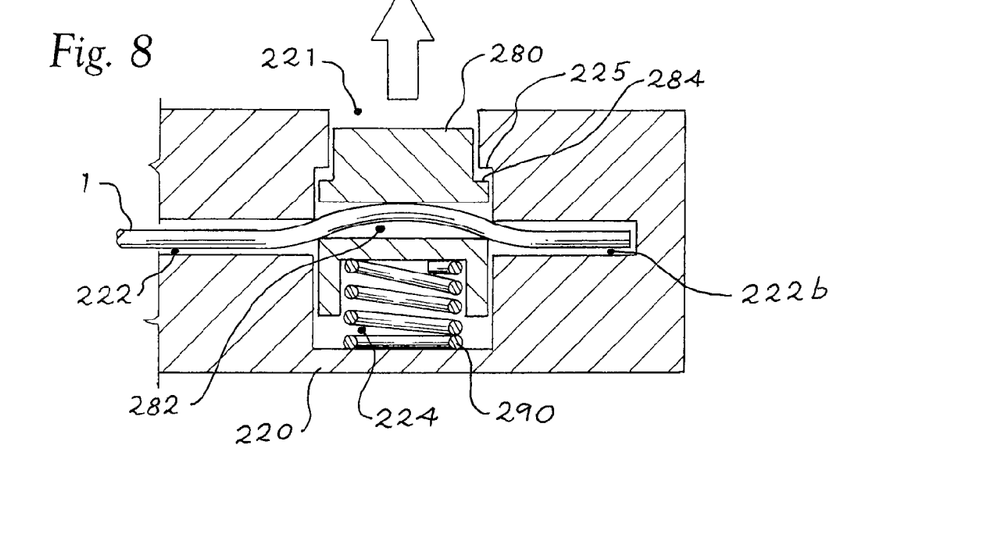
FIG. 8 is the view of FIG. 7 with the button released to retain the elongate device therewithin.

Turning now to FIGS. 6-8, another representative handle 200 configured to removably receive an elongate proximal portion 1 of a medical device is provided. The handle includes a housing 220 that defines a central lumen 222 extending from a distal surface of the housing 220 blindly along the either the entire length or a significant portion of the length of the housing 220. The lumen 222 and the distal opening into the lumen 222 is configured to receive an elongated proximal portion 1 of a medical device, such as a basket, snare, or the like to allow for a medical professional to ergonomically hold and manipulate the device within the patient. The housing 220 and lumen 222 are configured to receive the elongate portion 1 in a back loading manner, i.e. the proximal tip of the elongate portion 1 is threaded through the opening and lumen 222 and into the desired position within the housing 220.

The housing 220 further includes a movable button 280 that is disposed within a side opening in the housing 220 and is translatable within the housing 220 in both directions substantially perpendicular to the longitudinal axis 220a of the housing 220. The button 280 is received within a void 224 defined from the side opening 221 of the housing 220 and extending through the lumen 222 and to an opposite side of the housing 220 from the side opening 221. In some embodiments, the void 224 may include a stepped portion 225 where the cross-sectional area of the void 224 that extends through the lumen 222 (and for some desired distance on the opposite side of the lumen 222 from the side opening 221) is greater than the cross-sectional area of the side opening 221. In embodiments where the void 224 is substantially cylindrical (to receive a similarly sized cylindrical button 280) the radius of the portion of the void 224 crossing the lumen is larger than the radius of the concentric portion of the void 224 that defines the side hole 221. The step change in the size of the void 224 creates a step 225 that limits the outward motion of the button 280, in embodiments where the button 280 includes a ledge 284 that has a larger cross-sectional area than the area of the void at the side hole 221. Accordingly, in embodiments where the housing 220 and the button 280 are constructed with this geometry, the button 280 is free to partially move within the void 224, but prevented from leaving the handle through the side hole 221. Additionally, in some embodiments, the height of the button 280 (and more specifically the height of the button above the ledge 284) is smaller than the distance between the step 225 and the side hole 221, such that the button 280 is recessed within the void 224 to minimize or avoid inadvertent operation of the button 280 when holding or manipulating the handle 200. One or ordinary skill will appreciate upon review of this specification that the void 224 and button 280 may be formed from other profiles, such as squares, rectangles, and the like, as well as arcuate versions of these profiles to provide an ergonomic and high strength device.

The button 280 may be biased radially (i.e. in a direction toward the side hole 221) with a spring 290 or the like positioned within the void 224 and between a lower surface of the button 280 and an inner wall of the housing 220 within the void 224. The spring 290 may be constructed to urge the button 280 toward the side opening 221 as limited by contact between the step 225 and the ledge 284. The spring 290 is configured to be inwardly compressible (i.e. to allow the button to travel radially inward within the housing 220) when the top surface of the button 280 is pressed by the user through the side hole 221.

The button 280 further includes a button lumen 282 that extends through the width of the button 280, which is sized to accept and allow the proximal portion of a medical device configured to be used with the handle 200 to slide therethrough. The button lumen 282 is positioned upon the button 280 such that the button lumen 282 is not in registry (either complete registry or partial registry) with the lumen 222 of the housing 220 when the button 280 is in its normal position (i.e. the ledge 284 contacting the step 225 as urged by the spring 290). The button lumen 282 is configured such that the button lumen 282 is in substantially complete (or at least sufficient) registry with the handle lumen 222 when the button 280 is fully depressed by the user, which allows the proximal portion of the medical device to be completely threaded through the housing lumen 222, including the button lumen 282, and in some embodiments, a proximal lumen 222b disposed proximally in the housing 220 (i.e. the portion of the housing lumen 222 that the elongate medical device enters after being threaded through the button lumen 282).

The button 280 and button lumen 282 are configured such that there is some play for the button 280 to move slightly toward the side opening 221 of the housing 220 when the button 280 is released (due to the biasing force of the spring 290), such that the elongate portion 1 of the medical device exiting through the button lumen 282 (and in embodiments where the housing lumen 222 includes a proximal lumen 222b, both sides of the button lumen 282) is urged into contact with the upper edge of the housing lumen 222 and a portion of the upper surface of the button 280 that defines the button lumen 282, establishing a large normal force therebetween and therefore a high frictional connection between the two. Further, engagement of the proximal portion of the medical device with the housing lumen 222, the opposite edges of the button lumen 282, and in some embodiments the edge of the proximal lumen 222b increases the frictional force applied to the medical device to prevent release of the elongate medical device from the housing 220. In some representative embodiments, the proximal-most portion of the elongate portion 1 of the medical device may be sized such that it may be threaded from the housing lumen 222 into the button lumen 282 when the button 280 is fully depressed (FIG. 7) (established sufficient registry between the two lumens), but has a larger cross-sectional area than the opening into the button lumen 282 from the proximal portion of the housing lumen 222a, such that the proximal most portion of the elongate portion 1 cannot be pulled into the button lumen 282 (FIG. 8) until the button 280 is again fully compressed, eliminating the chance of inadvertent release of the device from the handle 200.

The elongate portion of the medical device may be released from the housing 220 by fully pressing the button 280 against the biasing force of the spring 290, which established at least sufficient registry between the housing lumen 222 and the button lumen 282 to minimize the frictional forces upon the medical device to allow it to be removed from the lumens by pulling the medical device from the lumens. When the medical device is fully withdrawn from the button lumen 282, the button 280 may be released, and the medical device may be fully withdrawn if warranted. Upon release of the button 280, the button 280 moves radially within the void 224 (as urged by the spring 290) until the ledge 284 of the button 280 engages the step 225 on the housing 220.

Figure 9:
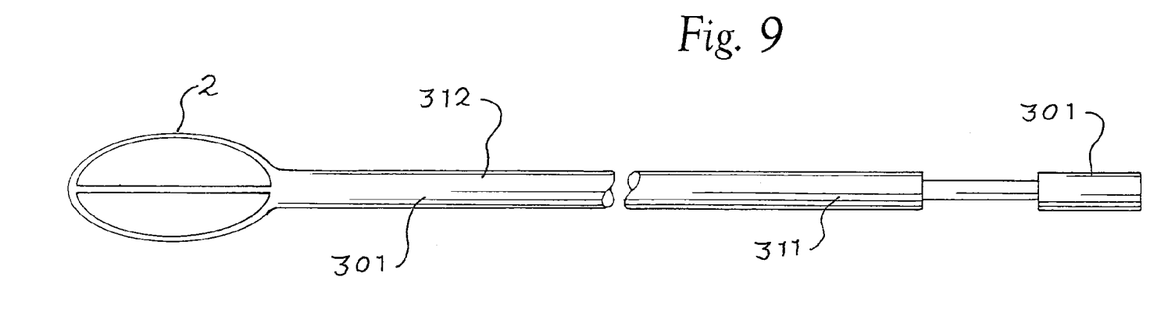
FIG. 9 is a side view of an alternate elongate portion of a medical device.

In some embodiments, the proximal portion an alternate elongate portion 301 of the medical device may be formed with a varying cross section, as shown in FIG. 9. Specifically, the proximal portion of the elongate portion 301 may include a proximal tip 310, a transition portion 311 just distal of the proximal tip 310, and a distal portion 312 that is distal of the transition portion 311. The transition portion 311 is configured to have a lower diameter along its length than both the distal portion 312 or the proximal tip 310. In most embodiments, the distal portion 312 and the proximal tip 310 will have the same diameter as each other and of the remainder of the elongate portion 301 of the medical device, while in other embodiments when needed or warranted, the distal portion 312 and the proximal tip 310 may include different diameters (both normally larger than the diameter of the transition portion 311).

Figure 10:
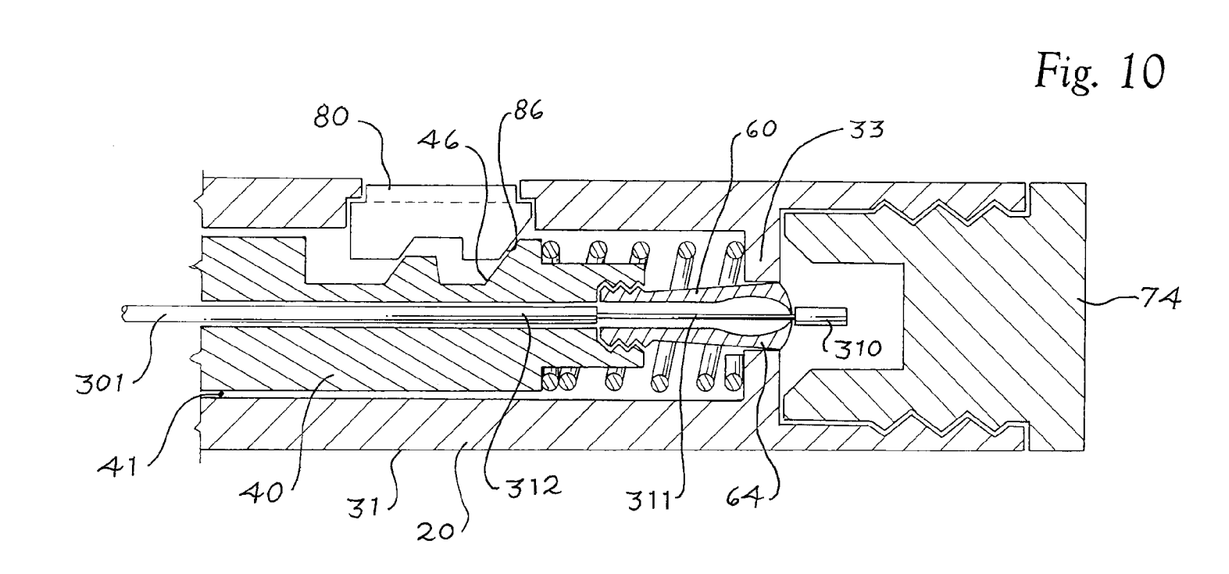
FIG. 10 is a cross-sectional view of the FIG. 2 showing receipt and engagement with the elongate portion depicted in FIG. 9.

In these embodiments, as shown in FIG. 10, the elongate portion 301 of the medical device and the housing 20 are configured such that the transition portion 311 is disposed within the collet 60 when the medical device is fully inserted into the handle 10, with the proximal tip 310 extending from the collet 60 and into the third portion 26 of the housing 20 (or proximally of the button 280 in those embodiments). The formation of the elongate portion 301 of the medical device in this manner provides for a step change in diameter that outside of the collett 60, which provides for additional strength to maintain the elongate portion 1 disposed within the housing in the normal configuration (i.e. the nominal configuration shown in FIG. 10), while minimizing the overall diameter of the elongate portion 1 to provide this step change. It can be appreciated that the housing 20 and alternate elongate portion 301 can be released from the housing by depressing the button 80 which translates the collet 60 and releases connection with the transition portion 311/proximal tip 310 in the same manner as depicted in FIG.

3 for the embodiment discussed above, which allows the elongate portion 301 to be removed from the handle 10.

Figure 11:
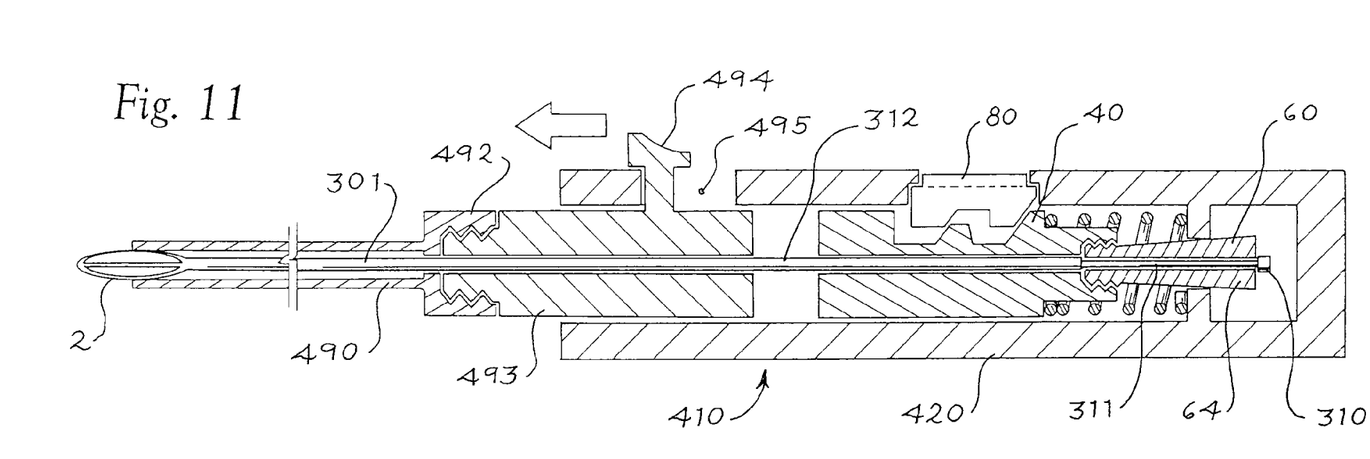
FIG. 11 is a cross-sectional view of an alternate handle that is configured to further manipulate a medical device, showing the medical device in a closed configuration.
Figure 12:
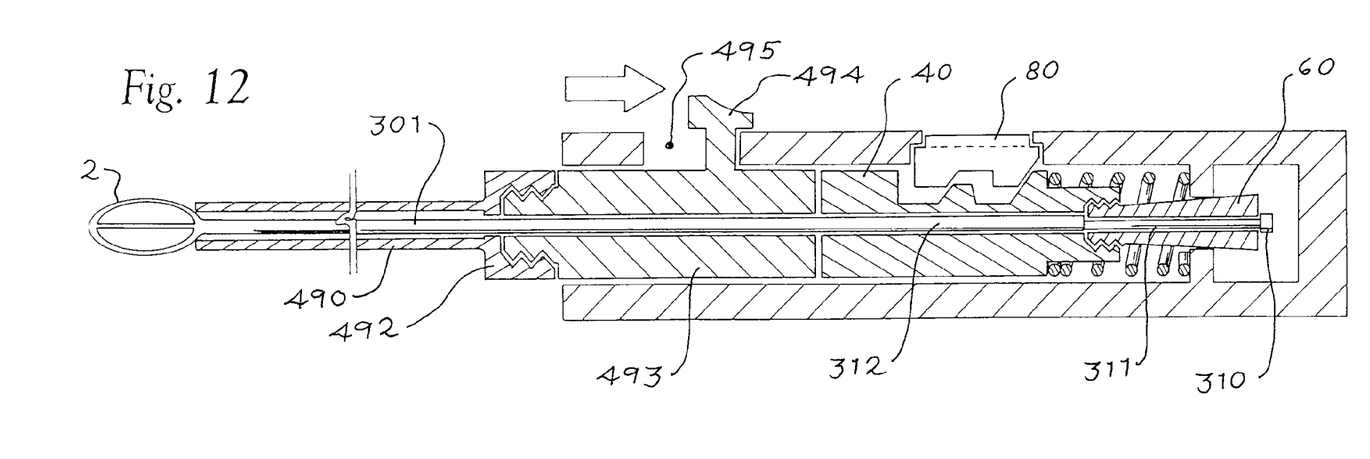
FIG. 12 is the handle of FIG. 11 showing the device in an open configuration.

Turning now to FIGS. 11 and 12, an alternate handle 410 may be provided that is fixably connected to an outer sheath 490 that is coaxially received about the portion of the elongate portion 301 (or 1, as discussed elsewhere herein) that extends from the handle 410. The outer sheath 490 is configured such that it may slide over all or a portion of the device 2 (such as a basket, snare, forceps, or the like) that is provided upon the distal end of the elongate portion 301 of the medical device to close the device, or minimize the diameter of the device for insertion, removal, or manipulation within the patient. The outer sheath 490 may be withdrawn proximally from the device such that the device is allowed to expand towards its normal configuration for operation within the patient.

The outer sheath 490 is fixed to a cap 492 that is movably fixed with respect to the housing 420 with a movable shaft 493 that extends into the distal portion of the housing 420. The movable shaft 493 receives a slider 494 that extends through a slot 495 defined in the housing 420 to allow the slider 494 to move proximally and distally with respect to the housing 420. For manufacturability purposes, the cap 492 and the slider 494 may be removably connectable to each other with a threaded connection, or the like, or they may fixably connectable, or monolithically formed together. As the slider 494 is moved distally within the slot 495, the outer sheath 490 moves distally toward the device, thereby compressing the device and covering at least a portion thereof (FIG. 11).

As the slider 494 is then urged proximally within the slot 495, the outer sheath 490 moves proximally with respect to the device, allowing the device to fully deploy to its normal biased configuration (FIG. 12). The remaining portions of the housing 420 may be constructed with structure described in the embodiments above, for example, such as with a button 80 and ramp surfaces 46, such that the collet 60 moves with respect to the elongate portion 301 to allow the elongate portion 301 to be released from the handle 10 when the button 80 is depressed.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

What is claimed:

1. A handle for removably receiving an elongate medical device, comprising:
    an elongate rigid housing enclosing a central hollow portion disposed along at least a substantial portion of the housing and an aperture disposed upon a side surface of the housing communicating with the hollow portion, the hollow portion maintaining a first inner diameter for a majority of a length of the hollow portion, and a second smaller inner diameter portion at a proximal portion of the hollow portion;
    a slidable core disposed within the hollow portion of the housing, the slidable core comprising an elongate core lumen disposed therethrough, the core lumen sized to receive a shaft of an elongate medical device, the core further comprising a ramp surface disposed thereon;
    a collet disposed within the hollow portion and movable with movement of the core within the housing, the collet comprising a collet lumen in registration with the core lumen, and further comprising two or more arms attached to a proximal end of the collet at a first portion thereon and each with a second portion that is biased radially outward outside of an outer surface of the collet,
    wherein the slidable core and the collet are biased distally such that the second portion of each arm contacts the smaller diameter portion to urge each arm radially inward from its biased configuration toward a restrained configuration,
    an elongate outer sheath movably fixed to the housing, a portion of the outer sheath extends into the central hollow portion of the housing and a second portion of the outer sheath extends distally outside of the central hollow portion, the outer sheath comprising a sheath lumen that is aligned coaxially with the elongate core lumen, the sheath lumen is sized to receive a distal portion of the shaft of the elongate medical device when received within the core lumen.

2. The handle of claim 1, wherein the elongate outer sheath is arranged is arranged to selectively cover and compress at least a portion of the elongate medical device that extends therethrough and to selectively allow the elongate medical device to extend distally out of the elongate outer sheath.

3. The handle of claim 1, further comprising a movable shaft fixed to the elongate outer sheath, the movable shaft includes a shaft lumen that is concentric with the core lumen, the movable shaft being disposed within the central hollow portion of the handle and slidable therein.

4. The handle of claim 3, further comprising a slider that extends radially from the movable shaft and through a slot in the housing to allow the slider to move proximally and distally with respect to the housing.

5. The handle of claim 4, further comprising a button disposed within the aperture and configured to be urged radially inward toward the core, wherein the slider and the button are capable of being independently operated.

6. The handle of claim 5, wherein the button has an inclined surface disposed thereon that makes surface to surface contact with the ramp surface upon the core, and wherein the incline and ramp surfaces are oriented such that radially inward motion of the button urges the core and collet in the proximal direction.

7. The handle of claim 6, wherein the contact between the incline surface and the ramp surface limits distal motion of the core within the handle as urged by a spring disposed within the hollow portion.

8. The handle of claim 6, wherein movement of the core and collet in the proximal direction removes the alignment between the arms and the second diameter portion of the hollow portion such that the second portions of each arm are free to move radially outward from the restrained configuration.

9. The handle of claim 1, wherein the arms each contribute to a rear opening into the collet lumen, wherein the motion of the arms radially outward increases a diameter of the rear opening.

10. The handle of claim 9, wherein the core lumen and the collet lumen are configured to slidably receive the shaft of an elongate medical device, such that a proximal end of the shaft extends through the rear opening.

11. The handle of claim 9, further comprising an elongate portion of a medical device provided as a kit with the handle, the elongate portion comprising a proximal tip, a transition portion connected distally of the proximal tip and formed with a smaller diameter than a diameter of the proximal tip, wherein the transition portion is configured to be received within the collet lumen, and the proximal tip extends through the rear opening.

12. The handle of claim 1, further comprising a elongate portion of a medical device provided as a kit with the handle comprising a working portion disposed distally of a shaft of the medical device, the working portion configured to be selectively covered and compressed by the elongate outer sheath and to selectively extend distally out of the elongate outer sheath.

13. The handle of claim 12, wherein the medical device further comprises a working portion disposed distally of the shaft, the working portion configured to be selectively covered and compressed by the elongate outer sheath and to selectively extend distally out of the elongate outer sheath.

14. A handle for receiving an elongate medical device, comprising:
 a housing defining an elongate hollow interior portion, the housing defined to allow communication with the interior portion through an open distal end and through an aperture disposed upon a side surface of the housing, the hollow portion defining a first portion proximate the distal end and the aperture, a second portion disposed proximally of the first portion with an inner diameter less than an inner diameter of the first portion, and a third portion disposed proximally of the second portion with an inner diameter larger than the inner diameter of the second portion;
 a core slidably disposed within the interior portion, comprising a central lumen disposed therethrough along a longitudinal axis of the core between a distal opening and a proximal opening, a ramp portion extending from an outer surface of the core at an oblique angle to the longitudinal axis, and two or more arms extending outwardly from a proximal end of the core and biased toward an extended configuration where a proximal end of each arm extends radially outside of an outer surface of the core, wherein the two or more arms combine to define the proximal opening; and
 a button movably disposed within the aperture substantially blocking communication with the hollow portion through the aperture, comprising an inclined surface that slidably engages the ramp surface, wherein engagement of the ramp and inclined surfaces establishes a normal position of the core within the housing, such that the arms are aligned with the second portion of the hollow portion to urge the arms inwardly away from their extended configuration and minimize the size of the proximal opening; and
 an elongate outer sheath movably fixed to the housing, a portion of the outer sheath extends into the central hollow portion of the housing and a second portion of the outer sheath extends distally outside of the central hollow portion, the outer sheath comprising a sheath lumen that is aligned coaxially with the central lumen, the sheath lumen is sized to receive a distal portion of the shaft of the elongate medical device when received within the central lumen.

15. The handle of claim 14, wherein the elongate outer sheath is arranged is arranged to selectively cover and compress at least a portion of the elongate medical device that extends therethrough and to selectively allow the elongate medical device to extend distally out of the elongate outer sheath.

16. The handle of claim 14, further comprising a movable shaft fixed to the elongate outer sheath, the movable shaft includes a shaft lumen that is concentric with the core lumen, the movable shaft being disposed within the hollow interior portion of the handle and slidable therein.

17. The handle of claim 16, further comprising a slider that extends radially from the movable shaft and through a slot in the housing to allow the slider to move proximally and distally with respect to the housing.

18. The handle of claim 14, wherein the button is configured such that radial inward motion thereof causes sliding contact between the incline and ramp surfaces, which urges the core proximally within the housing to position the arms within the third portion of the housing, thereby increasing the size of the proximal opening as the arms move radially outward toward their biased outward position.

19. The handle of claim 18, wherein the two or more arms are configured to engage a proximal end of the medical device disposed through the core lumen when the arms are aligned with the second portion of the housing, and the two or more arms disengage from the proximal end of the medical device when the arms move toward their biased outward position.

20. The handle of claim 19, wherein the proximal end of each arm includes a surface configured for contacting the proximal end of the medical device when the arms are aligned with the second portion of the hollow portion, to prevent motion of the medical device with respect to the core.

21. The handle of claim 14, further comprising a elongate portion of a medical device provided as a kit with the handle comprising a working portion disposed distally of a shaft of the medical device, the working portion configured to be selectively covered and compressed by the elongate outer sheath and to selectively extend distally out of the elongate outer sheath.

22. A handle for removably receiving an elongate medical device, comprising:
 an elongate rigid housing enclosing a central hollow portion disposed along at least a substantial portion of the housing and an aperture disposed upon a side surface of the housing communicating with the hollow portion, the hollow portion maintaining a first inner diameter for a majority of a length of the hollow portion, and a second smaller inner diameter portion at a proximal portion of the hollow portion;
 a slidable core disposed within the hollow portion of the housing, the slidable core comprising an elongate core lumen disposed therethrough, the core lumen sized to receive a shaft of an elongate medical device, the core further comprising a ramp surface disposed thereon;
 a collet disposed within the hollow portion and movable with movement of the core within the housing, the collet comprising a collet lumen in registration with the core lumen, and further comprising two or more arms attached to a proximal end of the collet at a first portion thereon and each with a second portion that is biased radially outward outside of an outer surface of the collet,
 wherein the slidable core and the collet are biased distally such that the second portion of each arm contacts the smaller diameter portion to urge each arm radially inward from its biased configuration toward a restrained configuration,
 wherein the arms each contribute to a rear opening into the collet lumen, wherein the motion of the arms radially outward increases a diameter of the rear opening, wherein the core lumen and the collet lumen are configured to slidably receive the shaft of an elongate medical device, such that a proximal end of the shaft extends through the rear opening, further comprising an elongate portion of a medical device provided as a kit with the handle, the elongate portion comprising a proximal tip, and a transition portion connected distally of the proximal tip and formed with a smaller diameter than a diameter of the proximal tip, wherein the transition portion is configured to be received within the collet lumen, and the proximal tip extends through the rear opening; and an elongate outer sheath movably fixed to the housing, a portion of the outer sheath extends into the central hollow portion of the housing and a second portion of the outer sheath extends distally outside of the central hollow portion, the outer sheath comprising a sheath lumen that is aligned coaxially with the elongate core lumen, the sheath lumen is sized to receive a distal portion of the shaft of the elongate medical device when received within the core lumen.

23. The handle of claim 22, wherein the elongate outer sheath is arranged is arranged to selectively cover and compress at least a portion of the elongate medical device that extends therethrough and to selectively allow the elongate medical device to extend distally out of the elongate outer sheath.

24. The handle of claim 22, further comprising a movable shaft fixed to the elongate outer sheath, the movable shaft includes a shaft lumen that is concentric with the core lumen, the movable shaft being disposed within the central hollow portion of the handle and slidable therein.

25. The handle of claim 24, further comprising a slider that extends radially from the movable shaft and through a slot in the housing to allow the slider to move proximally and distally with respect to the housing.

* * * * *

UNITED STATES PATENT AND TRADEMARK OFFICE
CERTIFICATE OF CORRECTION

PATENT NO. : 9,532,795 B2  
APPLICATION NO. : 14/490860  
DATED : January 3, 2017  
INVENTOR(S) : Shay J. Lavelle et al.

Page 1 of 1

It is certified that error appears in the above-identified patent and that said Letters Patent is hereby corrected as shown below:

In the Claims

In Column 12, Claim 2, Line 21, before "to selectively cover" delete "is arranged" (second occurrence).

In Column 13, Claim 15, Line 60, before "to selectively cover" delete "is arranged" (second occurrence).

In Column 16, Claim 23, Line 4, before "to selectively cover" delete "is arranged" (second occurrence).

Signed and Sealed this  
Fourth Day of April, 2017

Michelle K. Lee  
*Director of the United States Patent and Trademark Office*